US008903469B2

(12) United States Patent
Yamada et al.

(10) Patent No.: US 8,903,469 B2
(45) Date of Patent: Dec. 2, 2014

(54) DETERMINING VELOCITY OF CEREBROSPINAL FLUID BY MAGNETIC RESONANCE IMAGING

(75) Inventors: Shinya Yamada, Naka-gun (JP); Hitoshi Kanazawa, Utsunomiya (JP)

(73) Assignees: Tokai University Educational Systems, Tokyo (JP); Toshiba Medical Systems Corporation, Tochigi (JP)

( * ) Notice: Subject to any disclaimer, the term of this patent is extended or adjusted under 35 U.S.C. 154(b) by 594 days.

(21) Appl. No.: 12/572,761

(22) Filed: Oct. 2, 2009

(65) Prior Publication Data
US 2010/0087730 A1 Apr. 8, 2010

(30) Foreign Application Priority Data
Oct. 3, 2008 (JP) ................................ 2008-258963

(51) Int. Cl.
A61B 5/05 (2006.01)
G01R 33/563 (2006.01)
G06T 7/20 (2006.01)
G06T 5/50 (2006.01)
A61B 5/055 (2006.01)
G01R 33/56 (2006.01)
G01R 33/561 (2006.01)
A61B 5/00 (2006.01)

(52) U.S. Cl.
CPC .............. *A61B 5/055* (2013.01); *G01R 33/5608* (2013.01); *G01R 33/56316* (2013.01); *G06T 2207/30016* (2013.01); *G06T 7/208* (2013.01); G06T 2207/10088 (2013.01); G01R 33/5617 (2013.01); *G06T 5/50* (2013.01); G01R 33/5602 (2013.01); G06T 2207/20221 (2013.01); G01R 33/5616 (2013.01); A61B 5/7257 (2013.01)
USPC .......................................... 600/410; 600/407

(58) Field of Classification Search
USPC .......................................... 600/407, 410–423
See application file for complete search history.

(56) References Cited

U.S. PATENT DOCUMENTS 4,918,386 A * 4/1990 Dumoulin et al. ............ 324/309
4,958,637 A   9/1990 Aritomi
(Continued)

FOREIGN PATENT DOCUMENTS

JP        4-64343     2/1992
JP        7-116143    5/1995
(Continued)

OTHER PUBLICATIONS

Kurtcuoglu et al., Computational Investigation of Subject-Specific Cerebrospinal Fluid Flow in the Third Ventricle and Aqueduct of Sylvius, 2006, Journal of Biomechanics, pp. 1235-1245.*

(Continued)

*Primary Examiner* — James Kish
(74) *Attorney, Agent, or Firm* — Nixon & Vanderhye PC

(57) ABSTRACT

A velocity-image creating unit creates a velocity image that indicates a distribution of velocity components with respect to each of a plurality of images obtained by repeating a plurality of number of times Echo Planar Imaging (EPI) that is capable of obtaining velocity components of a Cerebrospinal Fluid (CSF) flowing inside a subject. A velocity-variance image creating unit calculates variance of velocity components along the time sequence by same position on velocity images by using a plurality of created velocity images. A superimposed-image processing unit then superimposes the distribution of the variance of the velocity components according to the velocity-variance image on an average absolute-value image, and an image display unit displays a superimposed image.

14 Claims, 13 Drawing Sheets

(56) References Cited

U.S. PATENT DOCUMENTS

| | | | |
|---|---|---|---|
| 5,281,914 A * | 1/1994 | Conturo et al. | 324/309 |
| 6,224,553 B1 * | 5/2001 | Nevo | 600/437 |
| 6,348,404 B1 | 2/2002 | Tabara et al. | |
| 6,438,404 B1 * | 8/2002 | Van Den Brink et al. | 600/419 |
| 8,315,450 B2 | 11/2012 | Quigley | |
| 2006/0119623 A1 | 6/2006 | Quigley | |
| 2008/0061780 A1 * | 3/2008 | Yamada et al. | 324/309 |

FOREIGN PATENT DOCUMENTS

| | | |
|---|---|---|
| JP | 10-234695 | 9/1998 |
| JP | 2001-252263 | 9/2001 |
| JP | 2003-516797 | 5/2003 |
| JP | 2007-20829 | 2/2007 |
| JP | 2008-67857 | 3/2008 |

OTHER PUBLICATIONS

Ståhlberg et al. A method for MR quantification of flow velocities in blood and CSF using interleaved gradient-echo pulse sequences. Magn Reson Imaging. Nov.-Dec. 1989;7(6):655-67. (Abstract).*

Thomsen et al. Fourier analysis of cerebrospinal fluid flow velocities: MR imaging study. The Scandinavian Flow Group. Radiology. Dec. 1990;177(3):659-65. (Abstract).*

Yamada et al., Non-Contrast Bulk Flow Imaging of Cerebrospinal Fluid (CSF) using Time-Spatial Labeling Inversion Pulse (time-SLIP), May 2008, International Society for Magnetic Resonance in Medicine, p. 1.*

Yamada, S et al., "Visualization of Cerebrospinal Fluid Movement with Spin Labeling at MR Imaging: Preliminary Results in Normal and Pathophysiologic Conditions", Radiology, vol. 249, No. 2, (Nov. 2008), pp. 644-652.

Bernstein, M.A. et al., "Handbook of MRI Pulse Sequences", Chapter 15.2, Phase Contrast, (2004), pp. 659-669.

Office Action dated Aug. 10, 2010 in JP Application No. 2008-258963 with English translation.

H. Kanazawa, et al., "Phase Contrast Rare for Slow Flow," Proc. Intl. Soc. Mag. Reson. Med., 1998, P2138.

Office Action dated Nov. 30, 2010 in JP Application No. 2008-258963 with English translation.

Office Action in U.S. Appl. No. 13/570,569, Yamada, et al., mailed Apr. 15, 2013.

Notice of Allowance in U.S. Appl. No. 13/570,569, mailed May 13, 2014.

* cited by examiner

EXCITED PORTION
(PLATE FORM)

I($r_a$, i)

US 8,903,469 B2

DETERMINING VELOCITY OF CEREBROSPINAL FLUID BY MAGNETIC RESONANCE IMAGING

CROSS-REFERENCE TO RELATED APPLICATIONS

This application is based upon and claims the benefit of priority from the prior Japanese Patent Application No. 2008-258963, filed on Oct. 3, 2008; the entire contents of which are incorporated herein by reference.

BACKGROUND

1. Technical Field

The present exemplary embodiment relates to an image processing apparatus, a magnetic resonance imaging apparatus, and an image processing method for processing an image obtained by imaging an inside of a subject. Particularly, the present exemplary embodiment relates to an image processing apparatus, a magnetic resonance imaging apparatus, and an image processing method according to which a distribution of velocity variations of a body fluid can be faithfully imaged even if the velocity variations of the fluid are not cyclical, such as velocity variations of a Cerebrospinal Fluid (CSF).

2. Related Art

As a conventional method of observing dynamics of a body fluid, such as CSF or blood, by using a magnetic resonance imaging apparatus, there is a method called "a phase contrast method" or "a phase shift method" that uses a flow-encode gradient magnetic field (for example, see Matt A. Bernstein, Kevin F. King, and Xiaohong Joe Zhou, "Handbook of MRI Pulse Sequences", Elsevier Academic Press, 2004, pp. 659-677).

FIG. 14 is a schematic diagram of a pulse sequence according to a conventional phase shift method. As shown in FIG. 14, usually, according to a phase shift method, a gradient echo method is used; and a phase shift proportional to a velocity is given to an image by applying a flow-encode gradient magnetic field (Gfe) (P3 shown in FIG. 14) between an excitation pulse (P1 shown in FIG. 14) and an echo signal (P2 shown in FIG. 14).

According to the phase shift method, it is basically assumed that subject velocity variations strongly correlate with an electrocardiogram waveform (ECG shown in FIG. 14). Precisely, as shown in FIG. 14, after a certain waiting time (Tdelay shown in FIG. 14) has elapsed since an R wave appearing on an electrocardiogram-gated waveform, a radio-frequency excitation is performed and then an echo signal is collected. To reconstruct one image, approximately 128 to 256 echo signals are usually required. Therefore, generally, according to the phase shift method, a procedure of collecting one echo signal with respect to each R wave is repeated 128 to 256 times by stepwisely changing a phase-encoding gradient magnetic-field pulse.

An image $S(r_a)$, which is obtained by performing reconstruction processing, such as a discrete Fourier transform, on the echo signals collected in this way, has a phase shift proportional to a velocity. A velocity image $V(r_a)$ indicating a distribution of velocities is obtained by performing processing on the image $S(r_a)$, for example, the processing being expressed by $V(r_a) = k(venc) \cdot \arg\{S(r_a)\}$ (where, $k(venc)$ denotes a proportional coefficient that changes in accordance with the shape of a pulse of the flow-encode gradient magnetic field), after performing correction processing because of imperfection of the apparatus or ununiformity of the static magnetic field.

However, when observing dynamics of a CSF by using the phase shift method, there are problems as described below.

For example, according to the phase shift method, an echo signal is collected with respect to each of a plurality of R waves, for example, 128 to 256 R waves, which are equivalent to time for approximately two-four minutes, and it is known that there is a fairly low correlation between velocity variations of an actual CSF and electrocardiogram gating. For this reason, the velocity of the CSF during collection of each echo signal fluctuates to a large extent, so that the velocity observed on a reconstructed image as a phase shift is just an average value of velocities while collecting echo signals.

Purposes of observing dynamics of a CSF vary, for example, there are a case of examining presence or absence of a CSF circulation, and a case of precisely examining whether traffic of a CSF is available into a space that seems closed at glance. In such case, to what extent the maximum velocity is, and how far a CSF in a certain portion reaches within a certain time are influential and meaningful, so that only an image of an average velocity in a relatively long time range obtained by the phase shift method is substantially insufficient. Moreover, according to the phase shift method, fluctuations in the velocity at the time of collecting each echo signal are large, consequently, ghost artifact tends to appear in the phase encoding direction on a reconstructed image, and the image quality has a limitation.

In addition to the phase shift method, there is a method of collecting an image within a relatively short time, such as one second, by using an Echo Planar Imaging (EPI) method, or a fast Spin Echo (SE) method (for example, see "Proc. of ISMRM (International Society of Magnetic Resonance in Medicine) 1998, No. 2138"). However, the method consumes time and efforts for reading images and is not practical, because images are not provided in a sorted manner for observing dynamics of a CSF, and a number of images have to be referred.

As described above, according to conventional methods, for example, the phase shift method, velocity variations of a body fluid that are not cyclical, such as velocity variations of a CSF, cannot be faithfully imaged.

BRIEF SUMMARY

According to one aspect of the present exemplary embodiment, an image processing apparatus includes a calculation-image creating unit that creates a calculation image including velocity components of a Cerebrospinal Fluid (CSF) flowing inside a subject with respect to each of a plurality of images obtained by repeating imaging a plurality of number of times according to an imaging method capable of obtaining the velocity components; a statistic-image creating unit that calculates statistics indicating velocity variation of the CSF by same position on calculation images by using a plurality of calculation images created by the calculation-image creating unit, and creates a statistic image indicating a distribution of calculated statistics; a statistics display unit that displays the distribution of the statistics according to the statistic image created by the statistic-image creating unit.

According to another aspect of the present exemplary embodiment, a magnetic resonance imaging apparatus includes a calculation-image creating unit that creates a calculation image including velocity components of a Cerebrospinal Fluid (CSF) flowing inside a subject with respect to each of a plurality of images obtained by repeating imaging a plurality of number of times according to an imaging method capable of obtaining the velocity components; a statistic-image creating unit that calculates statistics indicating velocity variation of the CSF by same position on calculation images by using a plurality of calculation images created by the calculation-image creating unit, and creates a statistic image indicating a distribution of calculated statistics; a statistics display unit that displays the distribution of the statistics according to the statistic image created by the statistic-image creating unit.

According to still another aspect of the present exemplary embodiment, a magnetic resonance imaging apparatus includes an imaging processing unit that performs flow imaging of acquiring a group of echo signals required for reconstructing one image with one excitation pulse with respect to an imaging region including a CSF, each time when a certain delay time elapses from each trigger signal that appears repeatedly; an image creating unit that creates a plurality of CSF images based on each group of echo signals obtained by the flow imaging performed by the imaging processing unit; and a display unit that continuously displays the CSF images created by the image creating unit.

According to still another aspect of the present exemplary embodiment, an image processing method comprising: creating a calculation image including velocity components of a CSF flowing inside a subject with respect to each of a plurality of images obtained by repeating imaging a plurality of number of times according to an imaging method capable of obtaining the velocity components; calculating statistics indicating velocity variation of the CSF by same position on calculation images by using a plurality of created calculation images, and creating a statistic image indicating a distribution of calculated statistics; and displaying the distribution of the statistics according to the statistic image.

DETAILED DESCRIPTION OF EXEMPLARY EMBODIMENTS

Exemplary embodiments of an image processing apparatus, a magnetic resonance imaging apparatus, and an image processing method according to the present invention will be explained below in detail with reference to the accompanying drawings. The following embodiments are explained below in cases where the embodiments according to the present invention are applied to a Magnetic Resonance Imaging apparatus (hereinafter, "an MRI apparatus").

Figure 1:
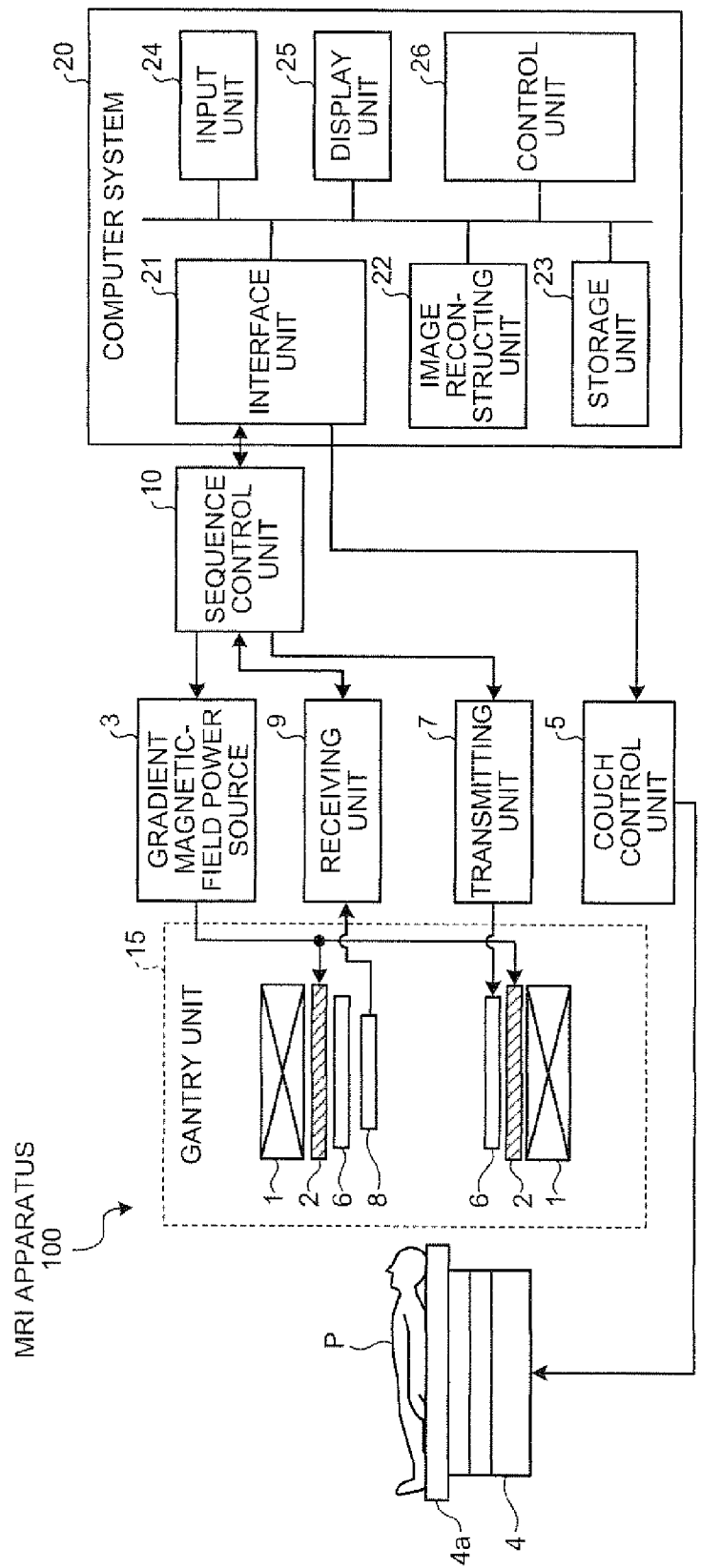
FIG. 1 is a schematic diagram of a general configuration of an MRI apparatus according to a first embodiment of the present invention.

First of all, a general configuration of an MRI apparatus according to a first embodiment of the present invention is explained below. FIG. 1 is a schematic diagram of a general configuration of the MRI apparatus according to the first embodiment. As shown in FIG. 1, an MRI apparatus 100 according to the first embodiment includes a static magnetic-field magnet 1, a gradient magnetic-field coil 2, a gradient magnetic-field power source 3, a couch 4, a couch control unit 5, a Radio Frequency (RF) transmitting coil 6, a transmitting unit 7, an RF receiving coil 8, a receiving unit 9, a sequence control unit 10, a gantry unit 15, and a computer system 20.

The static magnetic-field magnet 1 is a magnet formed in a hollow drum shape, and generates a uniform static magnetic field in its inside space. For example, a permanent magnet, or a super conducting magnet is used as the static magnetic-field magnet 1.

The gradient magnetic-field coil 2 is a coil formed in a hollow drum shape, and is arranged inside the static magnetic-field magnet 1. The gradient magnetic-field coil 2 is formed of three coils in combination corresponding to x, y, and z axes orthogonal to one another. The three coils generate gradient magnetic fields of which field intensities vary along three directions of the x, y, and z axes, respectively, by individually receiving a current supply from the gradient magnetic-field power source 3, which will be described later. It is assumed that the z axis direction is the same direction as that of the static magnetic field. The gradient magnetic-field power source 3 is a device that supplies a current to the gradient magnetic-field coil 2.

The gradient magnetic fields of the x, y, and z axes generated by the gradient magnetic-field coil 2 correspond to, for example, a slice-selective gradient magnetic field Gs, a phase-encoding gradient magnetic field Ge, and a readout gradient magnetic field Gr, respectively. The slice-selective gradient magnetic field Gs is used for arbitrarily setting a scan cross section. The phase-encoding gradient magnetic field Ge is used for changing the phase of an echo signal (a magnetic resonance signal) in accordance with a spatial position. The readout gradient magnetic field Gr is used for changing the frequency of an echo signal in accordance with a spatial position.

The couch 4 is a device that includes a table 4a on which a subject P is to be placed, and under the control of the couch control unit 5, which will be described later, the couch 4 inserts the table 4a on which the subject P is placed, into a hole (a scanning space) of the gradient magnetic-field coil 2. Usually, the couch 4 is placed such that the longitudinal direction of the couch 4 is to be parallel to the central axis of the static magnetic-field magnet 1. The couch control unit 5 is a device that controls the couch 4, and moves the table 4a in the longitudinal direction and upward and downward by driving the couch 4 under the control of the computer system 20.

The RE transmitting coil 6 is a coil arranged inside the gradient magnetic-field coil 2, and generates a radio-frequency magnetic field by receiving supply of a radio-frequency pulse from the transmitting unit 7. The transmitting unit 7 is a device that transmits a radio-frequency pulse corresponding to a Larmor frequency to the RE transmitting coil 6.

The RE receiving coil 8 is a coil arranged inside the gradient magnetic-field coil 2, and receives an echo signal emitted from the subject P owing to an influence of the radio-frequency magnetic field described above. Upon receiving an echo signal, the RF receiving coil 8 outputs the echo signal to the receiving unit 9.

The receiving unit 9 is a device that creates k-space data based on the echo signal output by the RI receiving coil 8. Specifically, the receiving unit 9 creates k-space data by converting an echo signal output from the IF receiving coil 8 into digital. The k-space data is associated with information about spatial frequencies of a PE direction, an RO direction, and an SE direction by the slice-selective gradient magnetic field Gs, the phase-encoding gradient magnetic field Ge, and the readout gradient magnetic field Gr. After creating k-space data, the receiving unit 9 transmits the k-space data to the sequence control unit 10.

The sequence control unit 10 is a device that performs scanning of the subject P by activating the gradient magnetic-field power source 3, the transmitting unit 7, and the receiving unit 9, based on sequence information transmitted from the computer system 20. The sequence information defines a procedure for scanning, such as the strength of power to be supplied to the gradient magnetic-field coil 2 by the gradient magnetic-field power source 3 and the timing of supplying the power, the strength of an IF signal to be transmitted to the RF transmitting coil 6 by the transmitting unit 7 and the timing of transmitting the RI signal, and the timing of detecting an echo signal by the receiving unit 9.

When k-space data is transmitted from the receiving unit 9 as a result of scanning the subject P by activating the gradient magnetic-field power source 3, the transmitting unit 7, and the receiving unit 9, the sequence control unit 10 transfers the k-space data to the computer system 20.

The gantry unit 15 includes the static magnetic-field magnet 1, the gradient magnetic-field coil 2, the RF transmitting coil 6, and the RF receiving coil 8; radiates a radio-frequency magnetic field onto a subject placed in the static magnetic field; and detects a Nuclear Magnetic Resonance (NMR) signal emitted from the subject.

The computer system 20 is a device that performs total control of the MRI apparatus 100, data collection, image reconstruction, and the like, and includes an interface unit 21, an image reconstructing unit 22, a storage unit 23, an input unit 24, a display unit 25, and a control unit 26.

The interface unit 21 controls input and output of various signals that are given and received to and from the sequence control unit 10. For example, the interface unit 21 transmits sequence information to the sequence control unit 10, and receives k-space data from the sequence control unit 10.

When having received k-space data, the interface unit 21 stores k-space data into the storage unit 23 with respect to each subject P.

The image reconstructing unit 22 creates spectrum data or image data of a desired nuclear spin inside the subject P by performing post-processing, i.e., reconstruction processing, such as Fourier transform processing, on k-space data stored in the storage unit 23. A configuration of the image reconstructing unit 22 will be explained later in detail.

The storage unit 23 stores k-space data received by the interface unit 21, and image data created by the image reconstructing unit 22, with respect to each subject P. A configuration of the storage unit 23 will be explained later in detail.

The input unit 24 is a device that receives various instructions and information input from an operator. As the input unit 24, a pointing device, such as a mouse or a trackball, a selecting device, such as a mode switch, and an input device, such as a keyboard, can be used as required.

The display unit 25 is a device that displays various information, such as spectrum data or image data, under the control of the control unit 26. A display device, such as a liquid crystal display, can be used as the display unit 25.

The control unit 26 includes a Central Processing Unit (CPU) and a memory, both of which are not shown, and carries out total control of the MRI apparatus 100. Specifically, the control unit 26 controls a scan by creating sequence information based on imaging conditions input by the operator via the input unit 24, and transmitting the created sequence information to the sequence control unit 10, and controls reconstruction of an image performed based on k-space data sent from the sequence control unit 10 as a result of the scan. A configuration of the control unit 26 will be explained later in detail.

Figure 2:
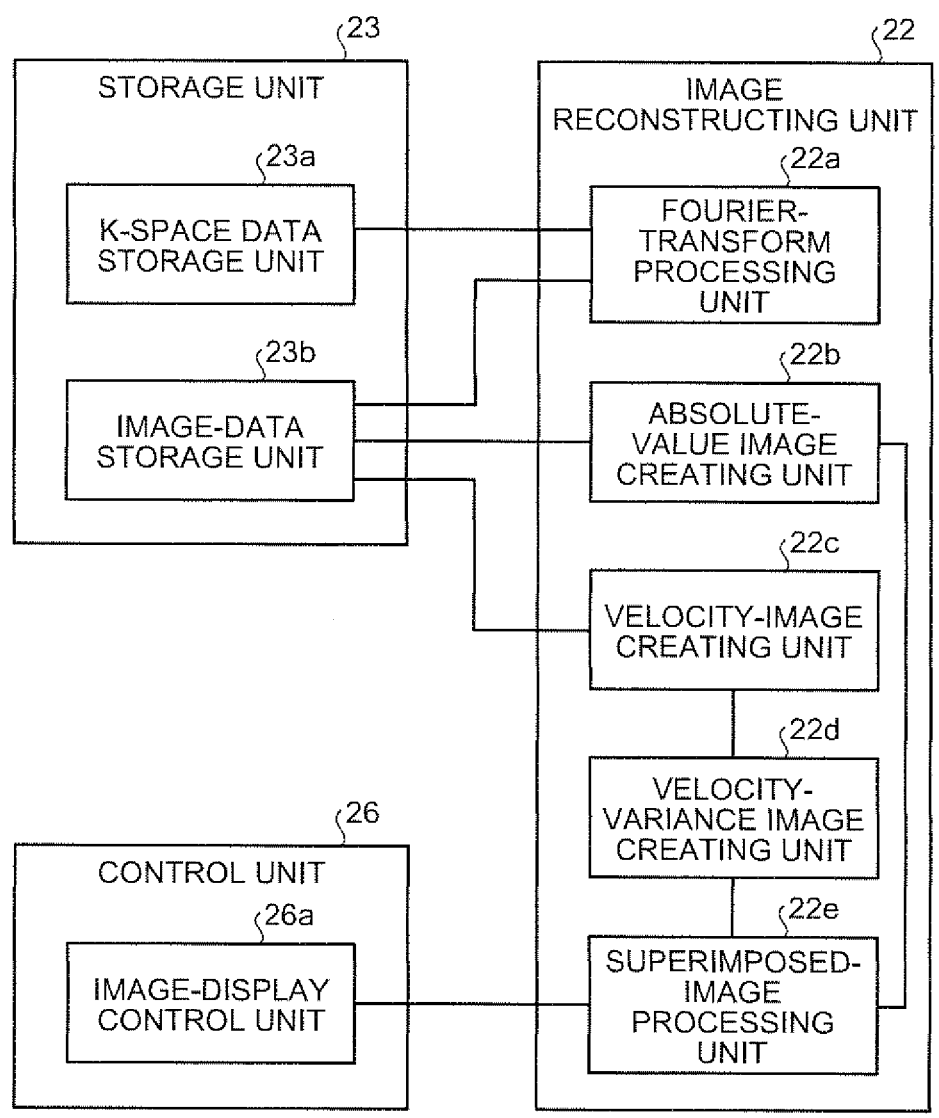
FIG. 2 is a functional block diagram of details of an image reconstructing unit, a storage unit and a control unit shown in FIG. 1.

A configuration of the image reconstructing unit 22, the storage unit 23, and the control unit 26 shown in FIG. 1 are explained below. FIG. 2 is a functional block diagram of a configuration of the image reconstructing unit 22, the storage unit 23, and the control unit 26 shown in FIG. 1.

As shown in FIG. 2, the storage unit 23 particularly includes a k-space data storage unit 23a, and an image-data storage unit 23b. The k-space data storage unit 23a stores k-space data received by the interface unit 21. The image-data storage unit 23b stores image data created by the image reconstructing unit 22.

The image reconstructing unit 22 particularly includes a Fourier-transform processing unit 22a, an absolute-value image creating unit 22b, a velocity-image creating unit 22c, a velocity-variance image creating unit 22d, and a superimposed-image processing unit 22e.

The Fourier-transform processing unit 22a reconstructs an image by performing reconstruction processing, such as a discrete two-dimensional Fourier transform, on k-space data stored in the k-space data storage unit 23a.

The first embodiment uses a plurality of images obtained by repeating imaging a plurality of number of times according to an imaging method that is capable of obtaining a velocity component of a body fluid flowing inside the subject. Specifically, the first embodiment uses a plurality of images obtained by repeating imaging a plurality number of times in a synchronized manner with an electrocardiogram waveform of the subject, according to the Echo Planar Imaging (EPI) method that is capable of reconstructing one image with one excitation pulse, and capable of giving a phase shift proportional to a velocity to the reconstructed image.

Figure 3:
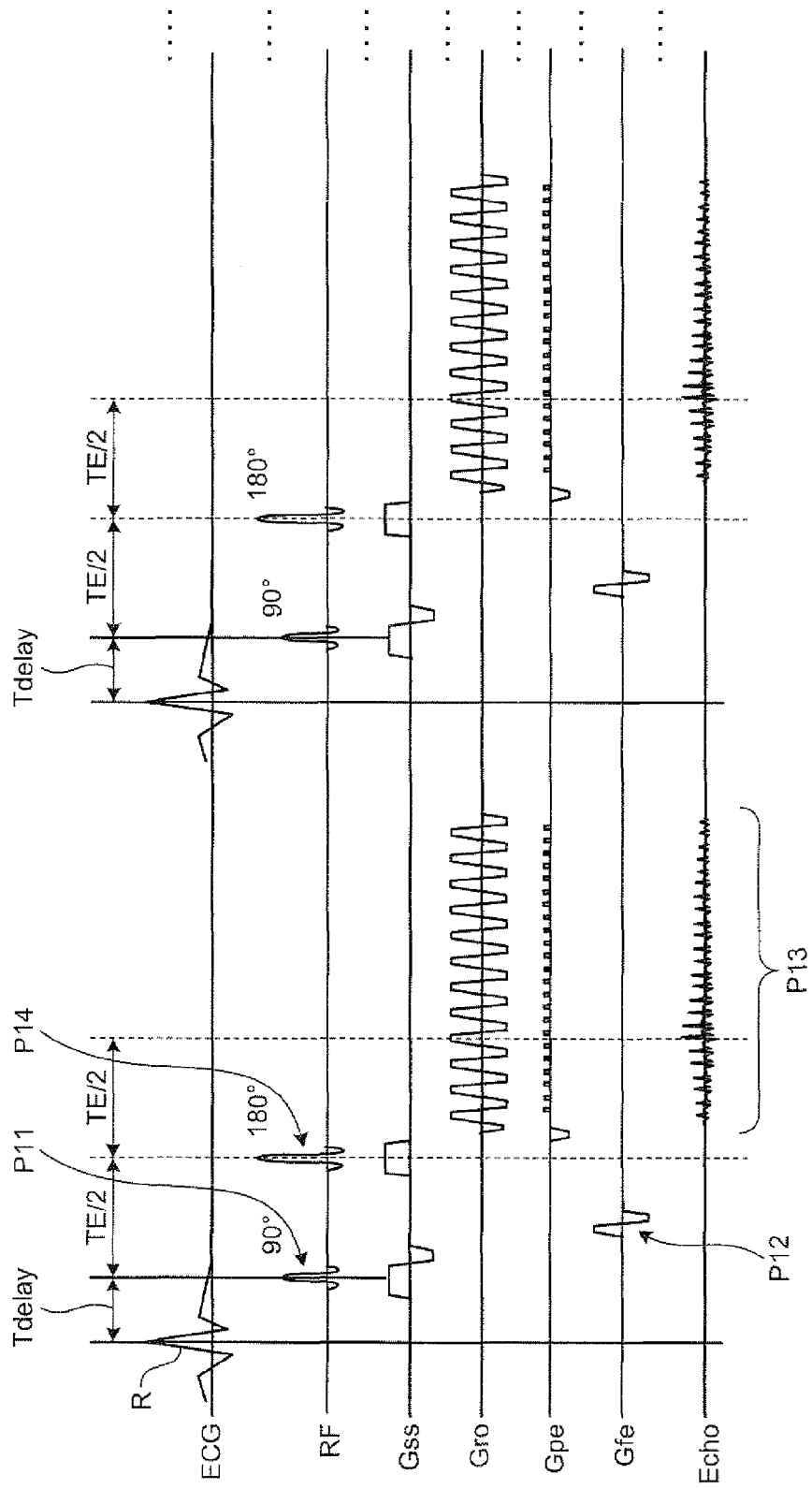
FIG. 3 is a schematic diagram of a pulse sequence according to an Echo Planar Imaging (EPI) method to be used in the first embodiment.

FIG. 3 is a schematic diagram of a pulse sequence according to the EPI, method used in the first embodiment. As shown in FIG. 3, according to the EPI method used in the first embodiment, the inside of a scan cross section is excited by applying a 90-degree excitation pulse (P11 shown in FIG. 3) after a certain waiting time (Tdelay shown in FIG. 3) has elapsed since an R wave appearing on an electrocardiogram waveform (ECG shown in FIG. 3). The phase of the obtained image shifts proportionally to the velocity of an imaging subject by applying a flow-encode gradient magnetic field (P12 shown in FIG. 3) between the 90-degree excitation pulse and the echo-signal collection (P13 shown in FIG. 3).

Although an EPI method of the Spin Echo (SE) type is described in FIG. 3 as an example, any of other imaging methods capable of obtaining a phase image can be used, for example, an EPI method of the Field Echo (FE) type. It is desirable to use an imaging method capable of obtaining an image for a time as short as possible. For example, an imaging method described in "Proc. of Annual Meeting, Society of Magnetic Resonance in Medicine, No. 2138, 1998," is an example of such method. Depending on an imaging method and the condition of an apparatus, it is desirable to perform a phase correction or another data correction processing in order to reduce a phase shift due to ununiformity of the static magnetic field or a spiral magnetic field.

Figure 4:
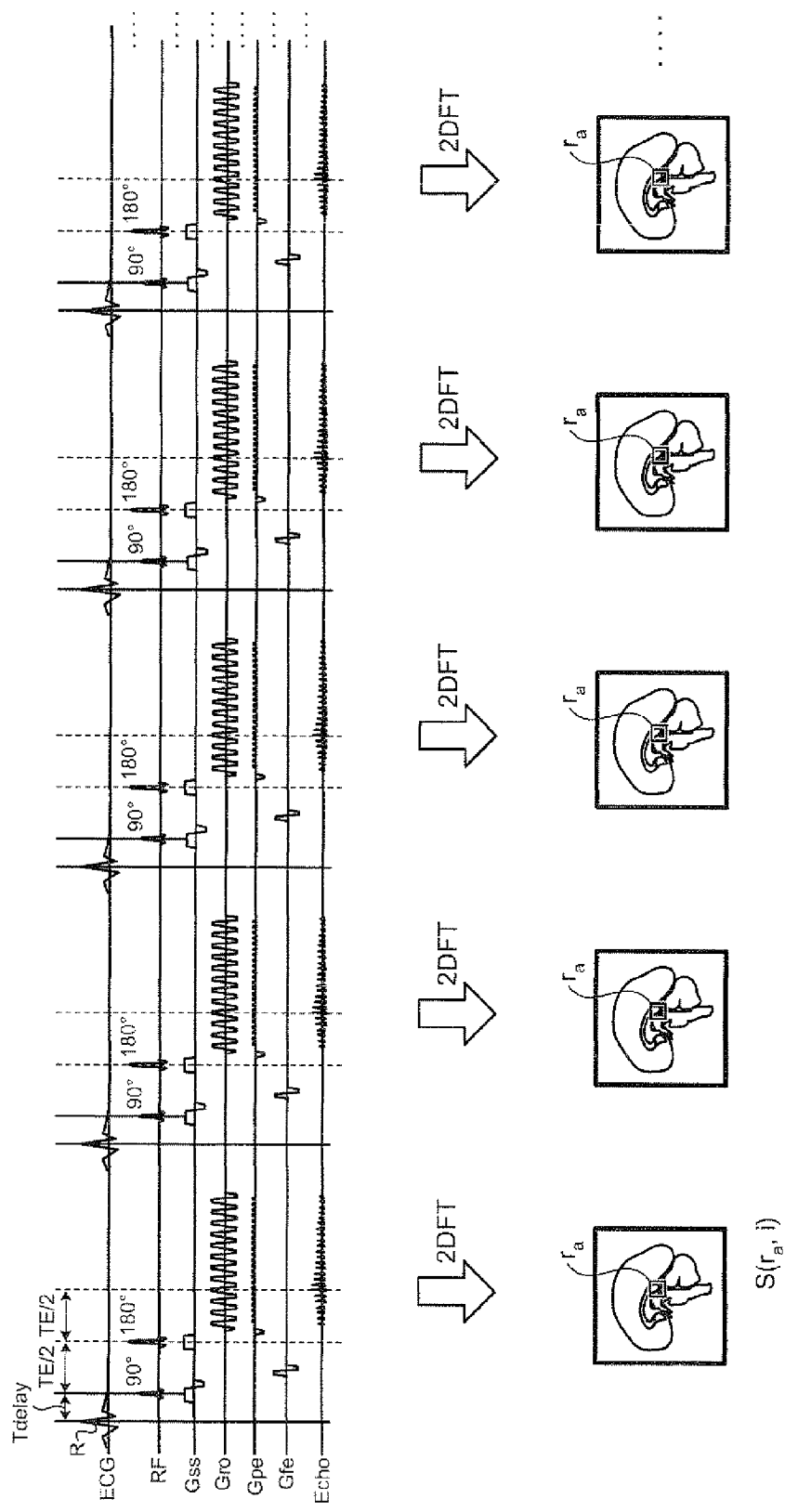
FIG. 4 is a schematic diagram of a flow of imaging according to the pulse sequence shown in FIG. 3.

FIG. 4 is a schematic diagram of a flow of imaging according to the pulse sequence shown in FIG. 3. As shown in FIG. 4, according to the pulse sequence shown in FIG. 3, a scan equivalent to one shot of the pulse sequence is performed after a certain waiting time (Tdelay shown in FIG. 4) has elapsed since an R wave appearing on the electrocardiogram waveform (ECG shown in FIG. 4).

According to the first embodiment, the Fourier-transform processing unit 22a reconstructs a plurality of images $S(r_a, i)$ as shown in FIG. 4 by performing reconstruction processing, such as a discrete two-dimensional Fourier transform, on respective k-space data of echo signals obtained through one shot as explained above. According to FIG. 4, $r_a$ denotes a vector that indicates a position on an image, and i denotes the order of collection. According to the images $S(r_a, i)$, the phase of a pixel shifts proportionally to the velocity.

The absolute-value image creating unit 22b creates absolute-value images from images reconstructed by the Fourier-transform processing unit 22a. Specifically, the absolute-value image creating unit 22b creates an absolute-value image $i(r_a, i)$ given by Expression (1) described below with respect to each of the images $S(r_a, i)$ reconstructed by the Fourier-transform processing unit 22a.

$$I(r_a,i)=\text{abs}\{S(r_a,i)\} \quad (1)$$

Furthermore, the absolute-value image creating unit 22b creates an average absolute-value image $I_{avg}(r_a)$ given by Expression (2) described below based on the created absolute-value images $I(r_a, i)$.

$$I_{avg}(r_a) = 1/N \cdot \sum_{i=1}^{N} \{I(r_a, i)\} \quad (2)$$

The velocity-image creating unit 22c creates calculation images that include a distribution of velocity components from images reconstructed by the Fourier-transform processing unit 22a. According to the first embodiment, the velocity-image creating unit 22c creates velocity images that indicate a distribution of velocity components as calculation images. Specifically, the velocity-image creating unit 22c creates a velocity image $V(r_a, i)$ given by Expression (3) described below with respect to each of the images $S(r_a, i)$ reconstructed by the Fourier-transform processing unit 22a. According to Expression (3), k(venc) denotes a proportional coefficient that varies in accordance with the shape of a pulse of the flow-encode gradient magnetic field.

$$V(r_a,i)=k(venc)\cdot\arg\{S(r_a,i)\} \quad (3)$$

Furthermore, the velocity-image creating unit 22c creates an average-velocity image $V_{avg}(r_a)$ given by Expression (4) described below based on the created velocity images $V(r_a, i)$.

$$V_{avg}(r_a) = 1/N \cdot \sum_{i=1}^{N} \{V(r_a, i)\} \quad (4)$$

The velocity-variance image creating unit 22d calculates statistics that indicate velocity variations of a body fluid by same position on the velocity images by using the velocity images created by the velocity-image creating unit 22c, and creates a statistic image that indicates a distribution of the calculated statistics. According to the first embodiment, the velocity-variance image creating unit 22d calculates variance of velocity components along the time sequence as statistics by using a phase shift, and creates a velocity-variance image that indicates a distribution of the variance of the velocity components, as a statistic image.

Specifically, the velocity-variance image creating unit 22d creates a velocity-variance image $V_{ari}, V(r_a)$ given by Expression (5) described below from the velocity images $V(r_a, i)$ and the average-velocity image $V_{avg}(r_a)$ created by the velocity-image creating unit 22c.

$$V_{ari}, V(r_a) = 1/N \cdot \sum_{i=1}^{N} \{V(r_a, i) - V_{avg}(r_a)\}^2 \quad (5)$$

The superimposed-image processing unit 22e creates a superimposed image that indicates the distribution of the variance of the velocity components according to the velocity-variance image created by the velocity-variance image creating unit 22d. Specifically, the superimposed-image processing unit 22e superimposes the distribution of the variance of the velocity components according to the velocity-variance image $V_{ari}, V(r_a)$ on the average absolute-value image $I_{avg}(r_a)$ created by the absolute-value image creating unit 22b.

When creating a superimposed image, the superimposed-image processing unit 22e changes a display mode of the distribution of the variance of velocity components in accordance with a value of the variance of the velocity components. For example, the superimposed-image processing unit 22e makes the average absolute-value image $I_{avg}(r_a)$ as a gray-scale image, and expresses the distribution of the variance of the velocity components according to the velocity-variance image $V_{ari}, V(r_a)$ with values of Red-Green-Blue (RGB) given by Expressions (6) to (8) described below. According to Expressions (6) to (8), "P, red" denotes the brightness of red, "P, green" denotes the brightness of green, and "P, blue" denotes the brightness of blue. In addition, kI and kV denote certain proportional coefficients respectively.

$$P,\text{red}=kI\cdot I_{avg}(r_a)+kV\cdot V_{ari}, V(r_a) \quad (6)$$

$$P,\text{green}=kI\cdot I_{avg}(r_a) \quad (7)$$

$$P,\text{blue}=kI\cdot I_{avg}(r_a) \quad (8)$$

Accordingly, the distribution of the variance of the velocity components is displayed in red on the superimposed image, and the brightness changes pixel by pixel in accordance with a value of the variance, so that the operator can easily grasp velocity variations of the body fluid. Although explained above is a case where the superimposed-image processing unit 22e expresses a distribution of variance of velocity components in red, it can be expressed in green or blue, for example.

Returning to FIG. 2, the control unit 26 particularly includes an image-display control unit 26a. The image-display control unit 26a displays a superimposed image created by the superimposed-image processing unit 22e.

Figure 5:
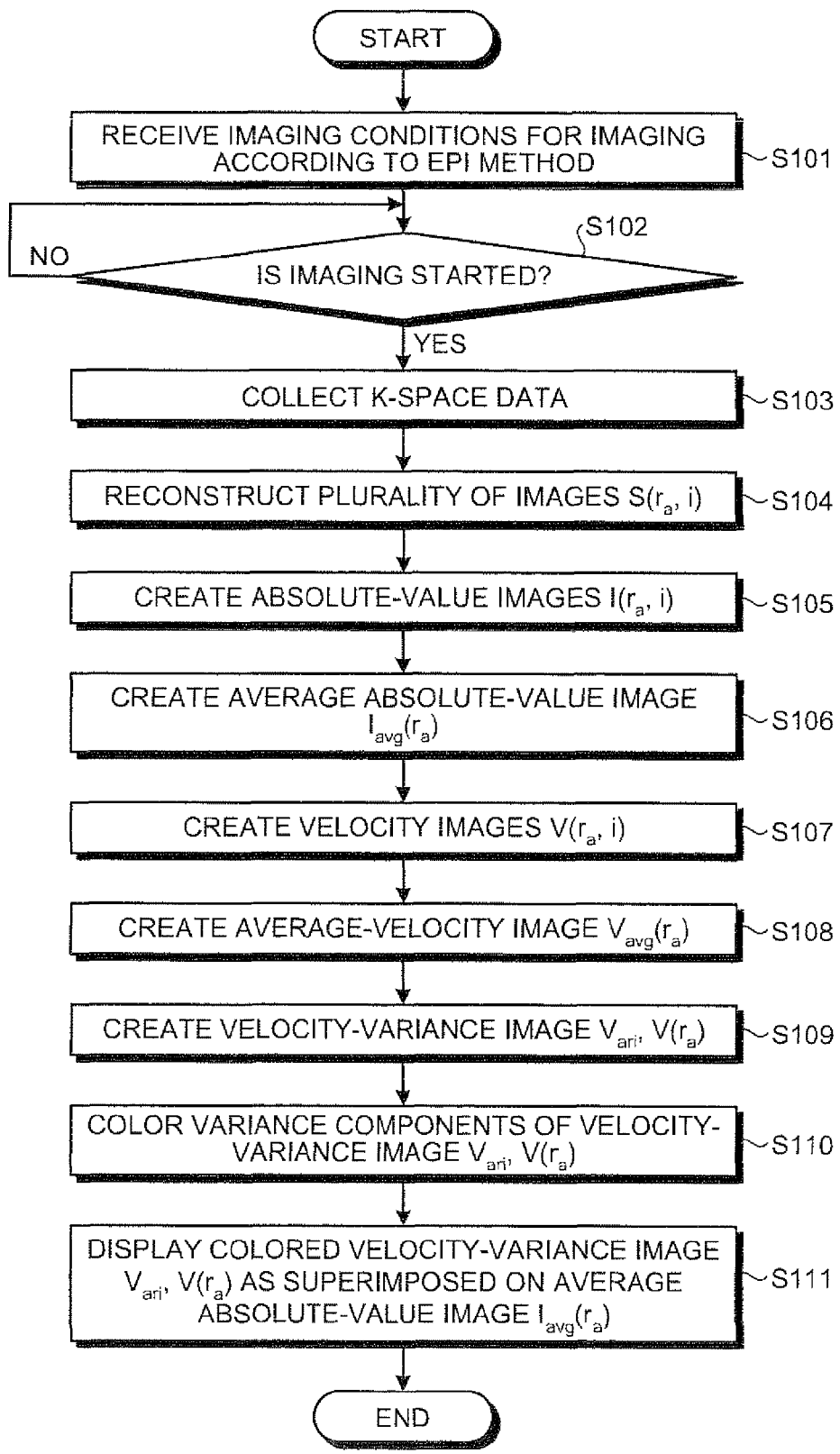
FIG. 5 is a flowchart of a process procedure of image processing performed by the MRI apparatus according to the first embodiment.
Figure 6:
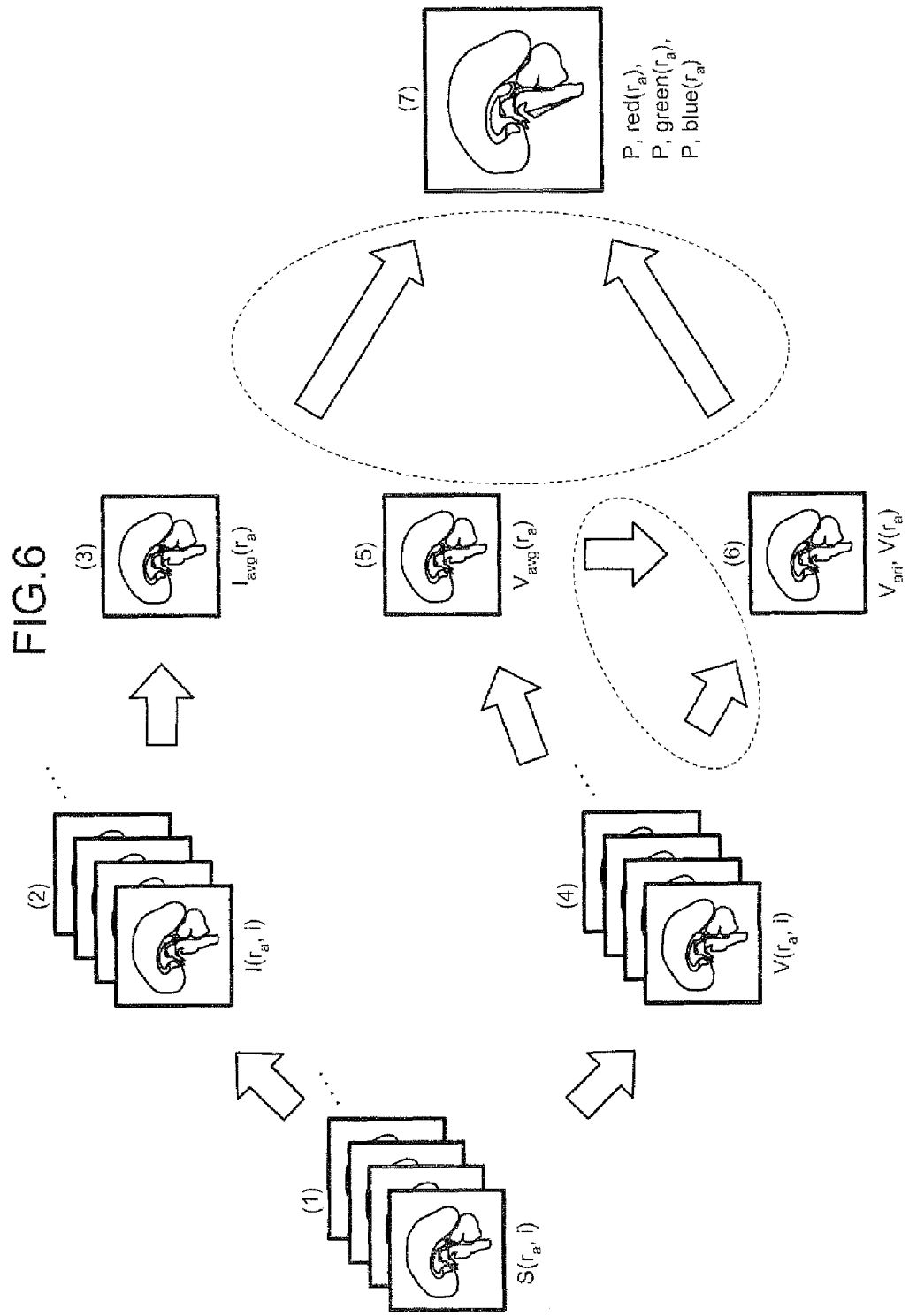
FIG. 6 is a schematic diagram of a flow of image creation performed by the MRI apparatus according to the first embodiment.

A process procedure of image processing performed by the MRI apparatus 100 according to the first embodiment is explained below. FIG. 5 is a flowchart of a process procedure of image processing performed by the MRI apparatus 100 according to the first embodiment; and FIG. 6 is a schematic diagram of a flow of image creation performed by the MFI apparatus 100 according to the first embodiment.

As shown in FIG. 5, according to the MRI apparatus 100, the control unit 26 receives imaging conditions for imaging according to the EPI method from the operator via the input unit 24 (Step S101). After that, when the start of imaging is instructed by the operator (Yes at Step S102), the control unit 26 creates sequence information about the pulse sequence according to the EPI method, transmits the created sequence information to the sequence control unit 10, and collects k-space data based on an echo signal (Step S103).

Subsequently, the Fourier-transform processing unit 22a reconstructs a plurality of images $S(r_a, i)$ as shown in section (I) in FIG. 6 by performing reconstruction processing, such as a discrete two-dimensional Fourier transform, on the collected k-space data (Step S104).

Subsequently, the absolute-value image creating unit 22b creates respective absolute-value images $I(r_a, i)$ as shown in section (2) in FIG. 6 with respect to the images $S(r_a, i)$ reconstructed by the Fourier-transform processing unit 22a (Step S105). Furthermore, the absolute-value image creating unit 22b creates an average absolute-value image $I_{avg}(r_a)$ as shown in section (3) in FIG. 6 based on the created absolute-value images $I(r_a, i)$ (Step S106).

On the other hand, the velocity-image creating unit 22c creates respective velocity images $V(r_a, i)$ as shown in section (4) in FIG. 6 with respect to the images $S(r_a, i)$ reconstructed by the Fourier-transform processing unit 22a (Step S107). Furthermore, the velocity-image creating unit 22c creates an average-velocity image $V_{avg}(r_a)$ as shown in section (5) in FIG. 6 based on the created velocity images $V(r_a, i)$ (Step S108).

Subsequently, the velocity-variance image creating unit 22d creates a velocity-variance image $V_{ari}, V(r_a)$ as shown in section (6) in FIG. 6 from the velocity images $V(r_a, i)$ and the average-velocity image $V_{avg}(r_a)$ created by the velocity-image creating unit 22c (Step S109).

The superimposed-image processing unit 22e then colors variance components of the velocity-variance image $V_{ari}, V(r_a)$ (Step S110), and superimposes the colored velocity-variance image $V_{ari}, V(r_a)$ on the average absolute-value image $I_{avg}(r_a)$ as shown in section (7) in FIG. 6; and then the image-display control unit 26a displays a superimposed image created by the superimposed-image processing unit 22e on the display unit 25 (Step S111).

As described above, according to the first embodiment, the velocity-image creating unit 22c creates a velocity image that indicates a distribution of velocity components with respect to each of a plurality of images obtained by repeating a plurality of number of times EPI that is capable of obtaining a velocity component of a body fluid flowing inside a subject.

The velocity-variance image creating unit 22d calculates variance of velocity components along the time sequence by same position on the velocity images, by using the velocity images created by the velocity-image creating unit 22c, and creates a velocity-variance image that indicates a distribution of variance of the calculated velocity components. The superimposed-image processing unit 22e then superimposes the distribution of the variance of the velocity components according to the velocity-variance image on an average absolute-value image, and the image-display control unit 26a displays a superimposed image on the display unit 25. In this way, according to the first embodiment, even if velocity variations of a body fluid are not cyclical, such as velocity variations of a CSF, a distribution of the velocity variations of the body fluid can be faithfully imaged.

Although the first embodiment is explained above in a case where the superimposed-image processing unit 22e uses an average absolute-value image $I_{avg}(r_a)$ as a grayscale image, an image obtained through another imaging can be used instead of for example. In such case, the superimposed-image processing unit 22e uses, for example, a $T_1$ weighted image or a $T_2$ weighted image.

Moreover, the first embodiment is explained above in a case where the superimposed-image processing unit 22e expresses a distribution of variance of velocity components in one color; and furthermore, it can be configured to change a display mode of the distribution of statistics in accordance with a direction of flowing of the body fluid. In such case, for example, similarly to the pulsed Doppler mode used in an ultrasound diagnosis apparatus, the superimposed-image processing unit 22e creates a two-dimensional blood-flow image by expressing the flowing direction of a blood flow with color information in red and blue, expressing the velocity of the blood flow with the brightness, and expressing variance of velocity components of the blood flow in green.

Figure 7:
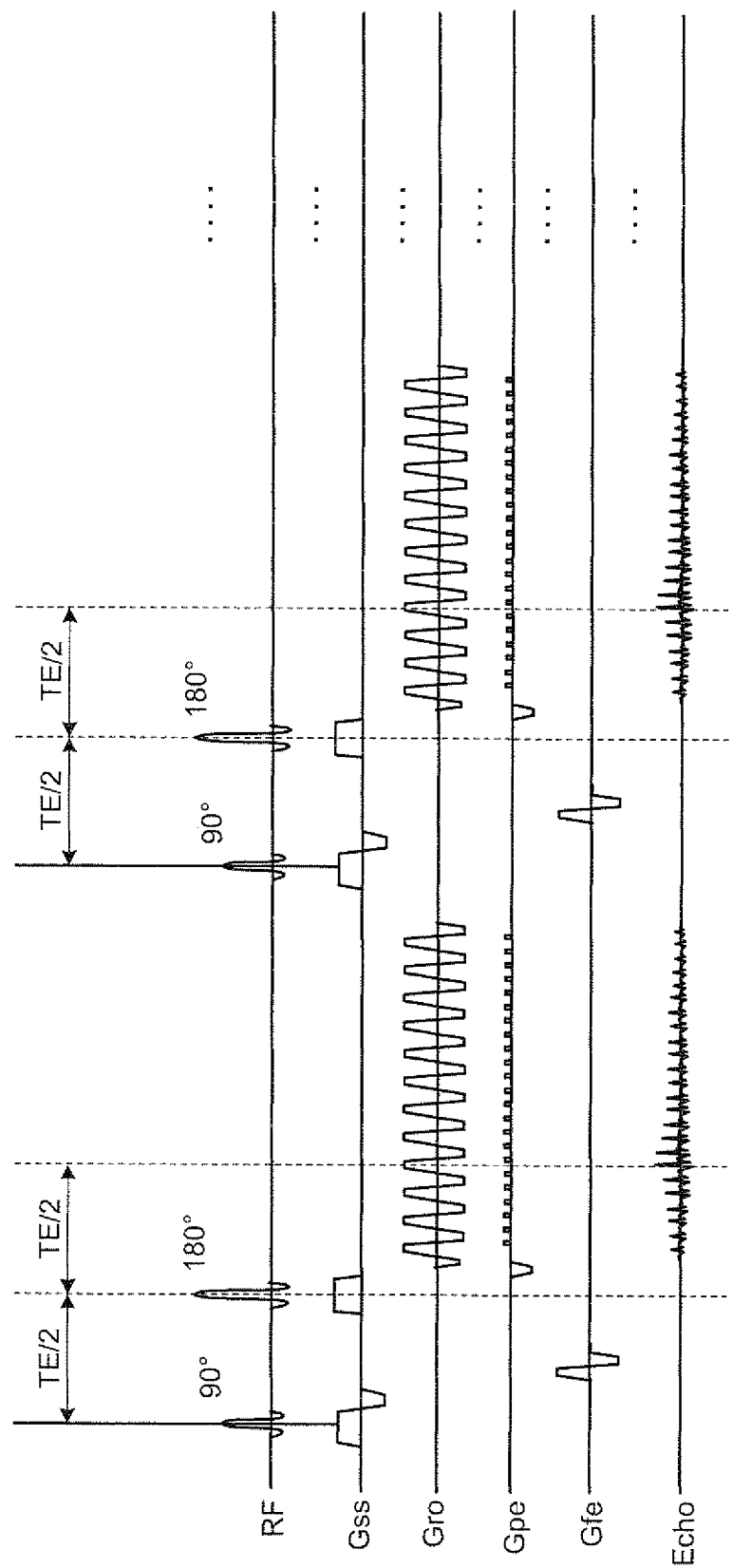
FIG. 7 is a schematic diagram of a modification of the pulse sequence to be used in the first embodiment.

Furthermore, the first embodiment is explained above in a case of using a plurality of images obtained by repeating imaging in a synchronized manner with an electrocardiogram waveform, (see FIG. 3); however, the present exemplary embodiments are not limited to this. FIG. 7 is a schematic diagram of a modification of the pulse sequence used in the first embodiment. For example, as shown in FIG. 7, it can be configured to use a plurality of images obtained by repeating imaging a plurality of number of times in a certain cycle without synchronizing with an electrocardiogram waveform. Because velocity variations of a CSF have a low correlation with electrocardiogram gating, there is little harm in collecting echo signals without synchronizing with electrocardiogram waveform. When repeating imaging in a certain cycle, a waiting time required in gated imaging (for example, Tdelay shown in FIG. 3) is not required, so that imaging can be performed for a shorter time.

Although the first embodiment is explained above in a case where a distribution of variance of velocity components is imaged by using a plurality of images obtained by repeating EPI using a flow-encode gradient magnetic field, the present exemplary embodiments are not limited to this. For example, it can be configured, to use an imaging method according to which a certain region present in a scan cross section is labeled by applying an inversion excitation pulse or a saturation excitation pulse, and then an image is reconstructed by detecting a signal of a body fluid flowing out from the region (for example, see JP-A 2001-252263 (KOKAI)).

A case of using such method is explained below as a second embodiment of the present invention. According to the second embodiment, such imaging method is referred to as a Time Spatial Labeling Inversion Pulse (Time-SLIP) method.

Moreover, the second embodiment is explained below in a case of using an inversion excitation pulse. A general configuration of an MRI apparatus according to the second embodiment is similar to that shown in FIG. 1, therefore explanation of it is omitted below, and details of an image reconstructing unit, a storage unit, and a control unit according to the second embodiment are explained below.

Figure 8:
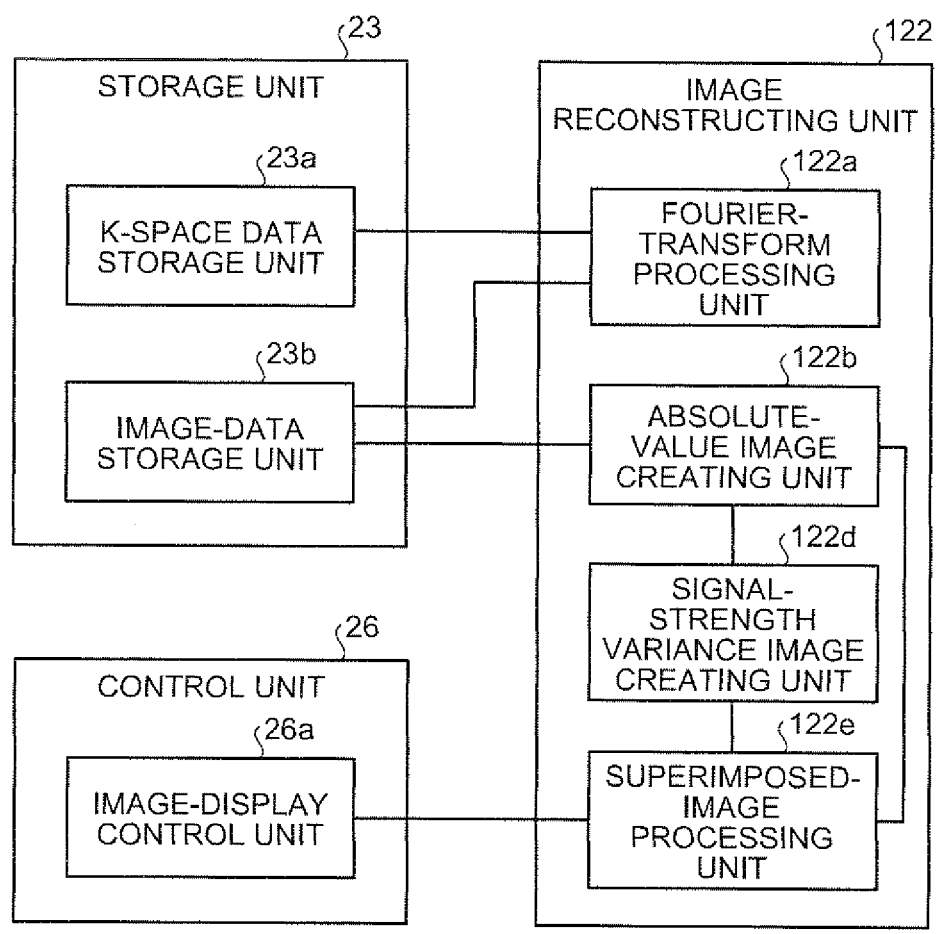
FIG. 8 is a functional block diagram of details of an image reconstructing unit, a storage unit, and a control unit according to a second embodiment of the present invention.

FIG. 8 is a functional block diagram of a configuration of the image reconstructing unit, the storage unit, and the control unit according to the second embodiment. For convenience of explanation, functional units that play roles similar to those of the units shown in FIG. 2 are assigned with the same reference numerals, and detailed explanations of them are omitted.

As shown in FIG. 8, an image reconstructing unit 122 according to the second embodiment particularly includes a Fourier-transform processing unit 122a, an absolute-value image creating unit 122b, a signal-strength variance image creating unit 122d, and a superimposed-image processing unit 122e.

The Fourier-transform processing unit 122a reconstructs an image by performing reconstruction processing, such as a discrete two-dimensional Fourier transform, on k-space data stored in the k-space data storage unit 23a.

Figure 9:
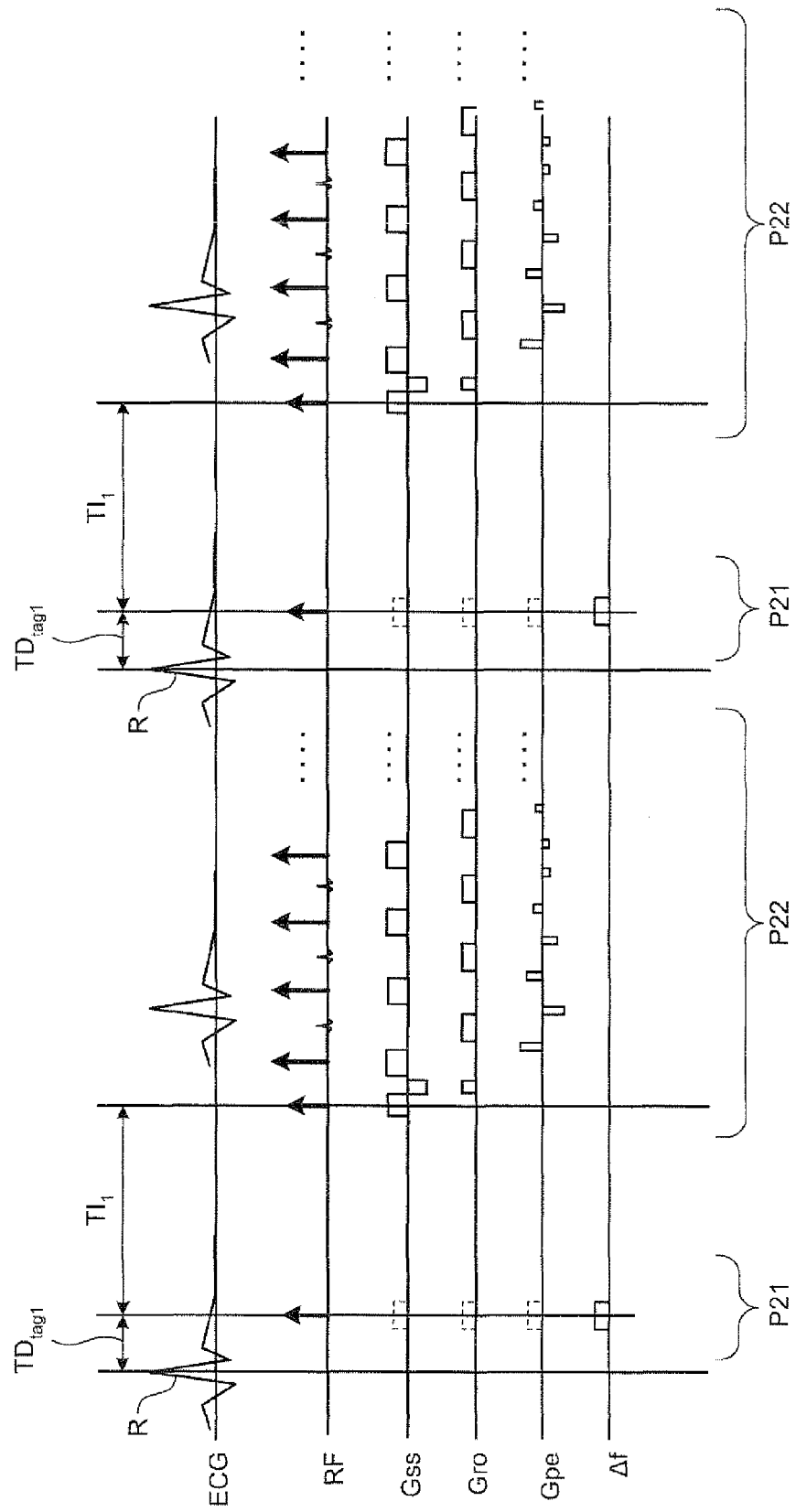
FIG. 9 is a schematic diagram of a pulse sequence according to a Time Spatial Labeling Inversion Pulse (Time-SLIP) method to be used in the second embodiment.

According to the second embodiment, the Time-SLIP method is used as an imaging method capable of obtaining a velocity component of a body fluid flowing inside a subject. FIG. 9 is a schematic diagram of a pulse sequence according to the Time-SLIP method used in the second embodiment; and FIG. 10 is a schematic diagram of an example of a position of labeling performed according to the Time-SLIP method according to the second embodiment.

Figure 10:
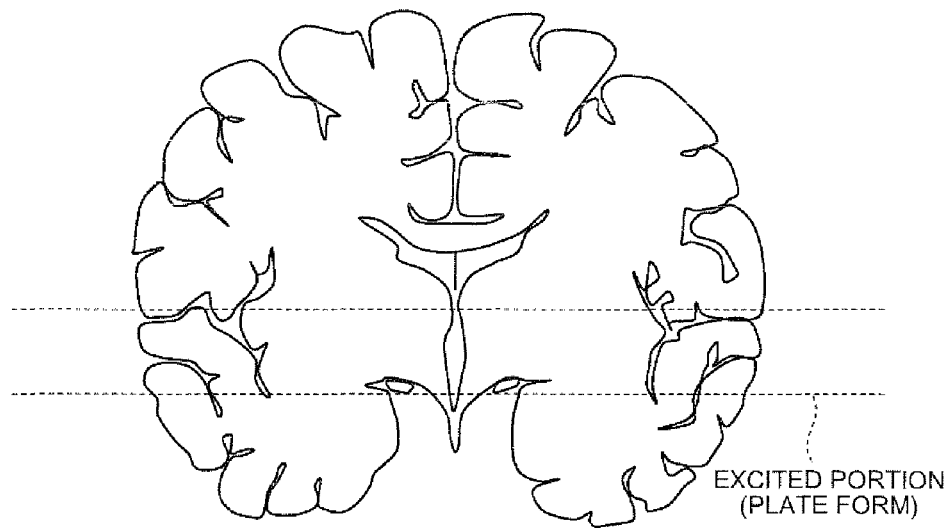
FIG. 10 is a schematic diagram of an example of a position of labeling performed by the Time-SLIP method according to the second embodiment.

As shown in FIG. 9, according to the Time-SLIP method used in the second embodiment, an Inversion Recovery (IR) pulse (P21 shown in FIG. 9) that inversely excites a certain region inside a scan cross section is applied, for example, as shown in FIG. 10, after a certain waiting time ($TD_{tag1}$ shown in FIG. 9) has elapsed since an R wave appearing on the electrocardiogram waveform (ECG shown in FIG. 9). When applying the IR pulse, an excitation frequency ($\Delta f$ shown in FIG. 9), and gradient magnetic fields of selective excitation (Gss, Gro, and Gpe shown in FIG. 9) are changed in accordance with an excitation position.

After a certain time ($TI_1$ shown in FIG. 9) has elapsed since then, echo signals required for reconstructing one image are collected (P22 shown in FIG. 9). FIG. 9 depicts a case of collecting echo signals by using the fast spin echo method. According to the Time-SLIP method used in the second embodiment, by repeating the collection a plurality of number of times, echo signals for a plurality of images are collected.

According to the second embodiment, the Fourier-transform processing unit 122a reconstructs a plurality of images $S(r_a, i)$ by performing reconstruction processing, such as a discrete two-dimensional Fourier transform, on respective k-space data of echo signals that are collected as described above.

The absolute-value image creating unit 122b creates absolute-value images that indicates a distribution of signal strengths from images reconstructed by the Fourier-transform processing unit 122a. Specifically, the absolute-value image creating unit 122b creates an absolute-value image $I(r_a, i)$ given by Expression (9) described below with respect to each of the images $S(r_a, i)$ reconstructed by the Fourier-transform processing unit 122a.

$$I(r_a, i) = \text{abs}\{S(r_a, i)\} \tag{9}$$

Figure 11:
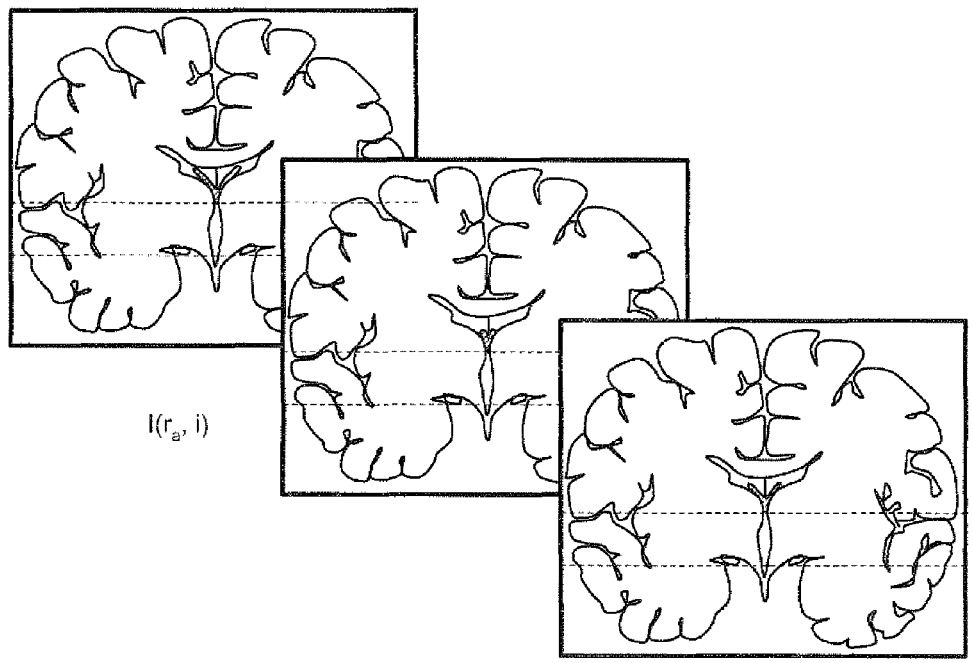
FIG. 11 is a schematic diagram of an example of absolute-value images created by an absolute-value image creating unit according to the second embodiment.

FIG. 11 is a schematic diagram of an example of the absolute-value images $I(r_a, i)$ created by the absolute-value image creating unit 122b according to the second embodiment. As shown in FIG. 11, although a CSF flowing out from a labeled region is imaged, velocities of the CSF when collecting echo signals to be bases for respective absolute-value images are different from one another, so that regions in which the signal strength is changed due to the CSF flowing out from the labeled region vary among the absolute-value images.

Furthermore, the absolute-value image creating unit 122b creates an average absolute-value image $I_{avg}(r_a)$ given by Expression (10) described below based on the created absolute-value images $I(r_a, i)$.

$$I_{avg}(r_a) = 1/N \cdot \sum_{i=1}^{N} \{I(r_a, i)\} \tag{10}$$

Returning to FIG. 8, the signal-strength variance image creating unit 122d calculates statistics that indicate velocity variations of the body fluid by same position on the absolute-value images by using the absolute-value images created by the absolute-value image creating unit 122b, and creates a statistic image that indicates a distribution of the calculated statistics. According to the second embodiment, the signal-strength variance image creating unit 122d calculates variance of signal strengths along the time sequence as statistics based on signal values of the body fluid, and creates a signal-strength variance image that indicates a distribution of the variance of the signal strengths, as a statistic image.

Specifically, the signal-strength variance image creating unit 122d creates a signal-strength variance image $V_{ari}, I(r_a)$ given by Expression (11) described below from the absolute-value images $I(r_a, i)$ and the average absolute-value image $I_{avg}(r_a)$ created by the absolute-value image creating unit 122b.

$$V_{ari}, I(r_a) = 1/N \cdot \sum_{i=1}^{N} \{I(r_a, i) - I_{avg}(r_a)\}^2 \tag{11}$$

The superimposed-image processing unit 122e creates a superimposed image that indicates the distribution of the variance of the signal strengths according to the signal-strength variance image created by the signal-strength variance image creating unit 122d. Specifically, the superimposed-image processing unit 122e superimposes the distribution of the variance of the signal strengths according to the signal-strength variance image $V_{ari}, I(r_a)$ on the average absolute-value image $I_{avg}(r_a)$ created by the absolute-value image creating unit 122b.

When creating a superimposed image, the superimposed-image processing unit 122e changes a display mode of the distribution of the variance of the signal strengths in accordance with a value of the variance of the signal strengths. For example, the superimposed-image processing unit 122e makes the average absolute-value image $I_{avg}(r_a)$ as a grayscale image, and expresses the distribution of the variance of the signal strengths according to the signal-strength variance image $V_{ari}, I(r_a)$ with values of Red-Green-Blue (ROB) given by Expressions (12) to (14) described below. According to Expressions (12) to (14), "P, red" denotes the brightness of red, "P, green" denotes the brightness of green, and "P, blue"

denotes the brightness of blue. In addition, kI and kV denote certain proportional coefficients respectively.

$$P,\text{red}=kI \cdot I_{avg}(r_a)+kV \cdot V_{ari}I(r_d) \quad (12)$$

$$P,\text{green}=kI \cdot I_{avg}(r_a) \quad (13)$$

$$P,\text{blue}=kI \cdot I_{avg}(r_a) \quad (14)$$

Accordingly, the distribution of the variance of the signal strengths is displayed in red on the superimposed image, and the brightness changes pixel by pixel in accordance with a value of the variance, so that the operator can easily grasp change in the signal strength due to a flow of the body fluid. Although explained above is a case where the superimposed-image processing unit 122e expresses a distribution of variance of signal strengths in red, it can be expressed in green or blue, for example.

Figure 12:
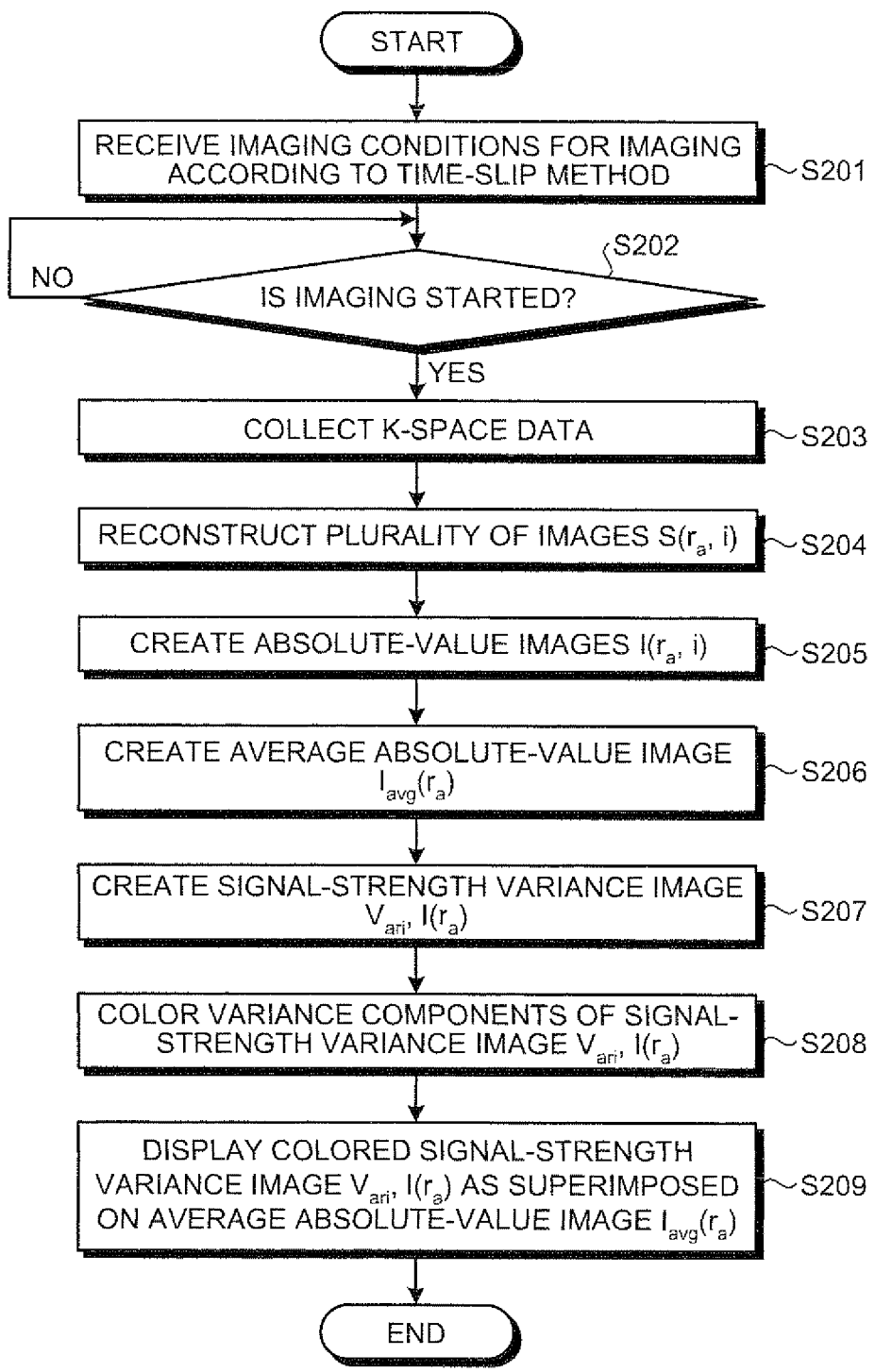
FIG. 12 is a flowchart of a process procedure of image processing performed by an MRI apparatus according to the second embodiment.
Figure 13:
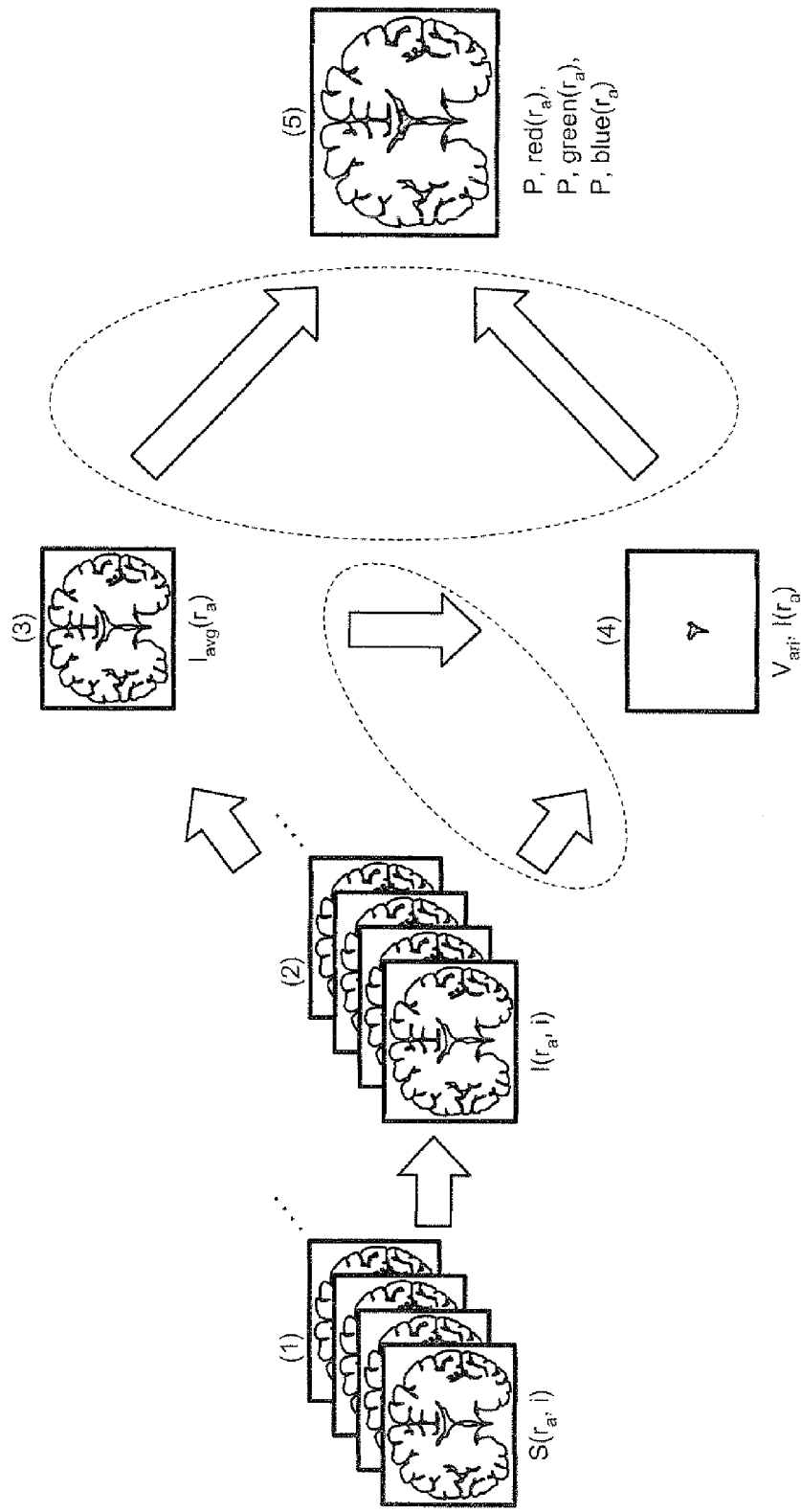
FIG. 13 is a schematic diagram of a flow of image creation performed by the MRI apparatus according to the second embodiment.
Figure 14:
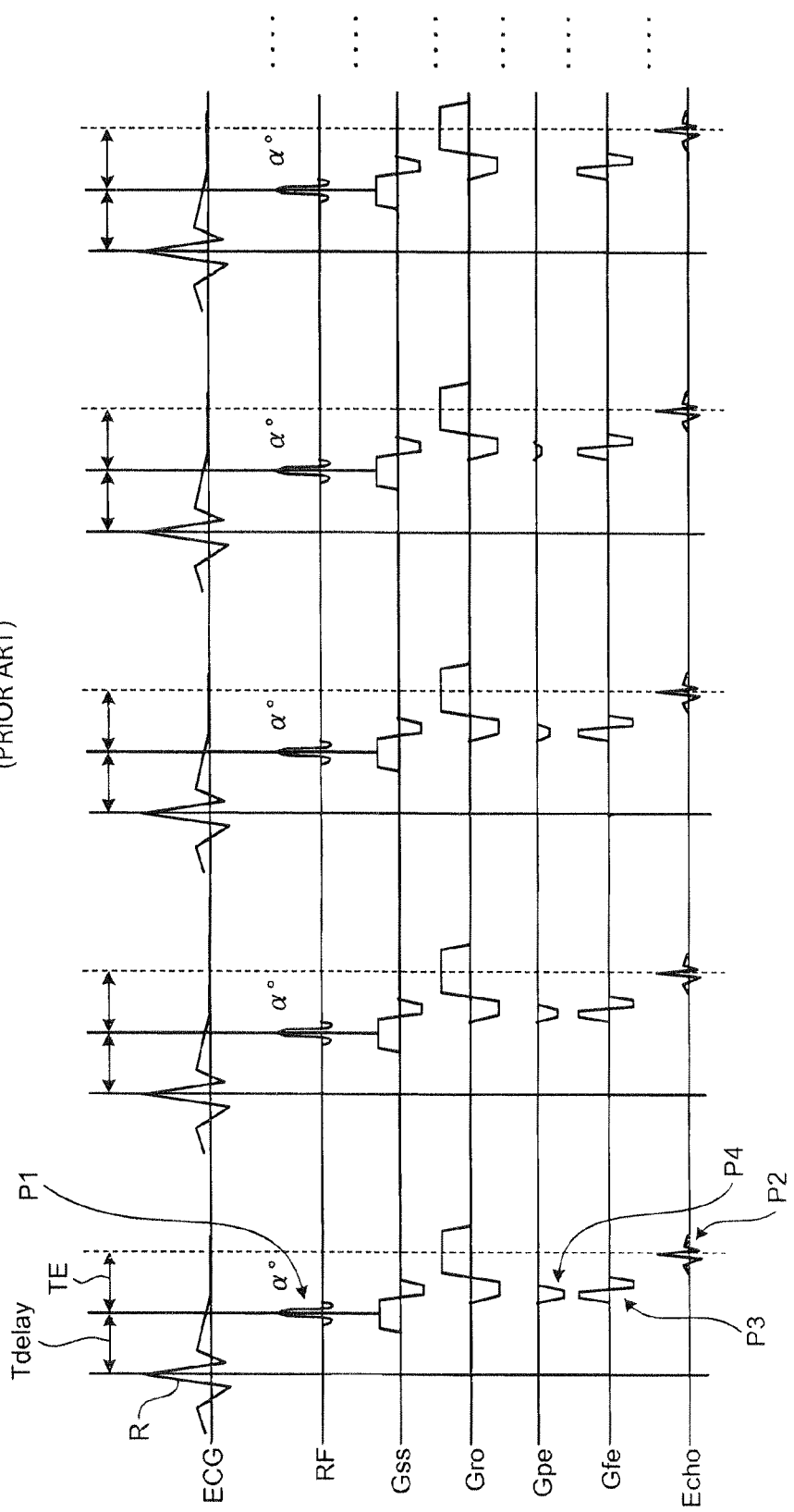
FIG. 14 is a schematic diagram of a pulse sequence according to a conventional phase shift method.

A process procedure of image processing performed by the MRI apparatus 100 according to the second embodiment is explained below. FIG. 12 is a flowchart of a process procedure of image processing performed by the MRI apparatus 100 according to the second embodiment; and FIG. 13 is a schematic diagram of a flow of image creation performed by the MRI apparatus 100 according to the second embodiment.

As shown in FIG. 12, according to the MRI apparatus 100, the control unit 26 receives imaging conditions for imaging according to the Time-SLIP method from the operator via the input unit 24 (Step S201). After that, when the start of imaging is instructed by the operator (Yes at Step S202), the control unit 26 creates sequence information about the pulse sequence according to the Time-SLIP method, transmits the created sequence information to the sequence control unit 10, and collects k-space data based on an echo signal (Step S203).

Subsequently, the Fourier-transform processing unit 122a reconstructs a plurality of images $S(r_a, i)$ as shown in section (1) in FIG. 13 by performing reconstruction processing, such as a discrete two-dimensional Fourier transform, on the collected k-space data (Step S204).

Subsequently, the absolute-value image creating unit 122b creates respective absolute-value images $I(r_a, i)$ as shown in section (2) in FIG. 13 with respect to the images $S(r_a, i)$ reconstructed by the Fourier-transform processing unit 122a (Step S205). Furthermore, the absolute-value image creating unit 122b creates an average absolute-value image $I_{avg}(r_a)$ as shown in section (3) in FIG. 13 based on the created absolute-value images $I(r_a, i)$ (Step S206).

The signal-strength variance image creating unit 122d then creates a signal-strength variance image $V_{ari}, I(r_a)$ as shown in section (4) in FIG. 13 from the absolute-value images $I(r_a, i)$ and the average absolute-value image $I_{avg}(r_a)$ created by the absolute-value image creating unit 122b (Step S207).

The superimposed-image processing unit 122e then colors variance components of the signal-strength variance image $V_{ari}, I(r_a)$ (Step S208), and superimposes the colored signal-strength variance image $V_{ari}, I(r_a)$ on the average absolute-value image $T_{avg}(r_a)$ as shown in section (5) in FIG. 13; and then the image-display control unit 26a displays a superimposed image created by the superimposed-image processing unit 122e on the display unit 25 (Step S209).

As described above, according to the second embodiment, the absolute-value image creating unit 122b creates an absolute-value image that indicates a distribution of signal strengths with respect to each of a plurality of images obtained by the Time-SLIP method of reconstructing an image by detecting a signal of a body fluid flowing out from a labeled region. The signal-strength variance image creating unit 122d calculates variance of signal strengths along the time sequence by same position on the absolute-value images by using the created absolute-value images, and creates a signal-strength variance image that indicates a distribution of variance of the calculated signal strengths. The superimposed-image processing unit 122e then superimposes the distribution of the variance of the signal strengths according to the signal-strength variance image on an average absolute-value image, and the image-display control unit 26a displays a superimposed image on the display unit 25. In this way, according to the second embodiment, similarly to the first embodiment, even if velocity variations of a body fluid are not cyclical, such as velocity variations of a CSF, a distribution of the velocity variations of the body fluid can be faithfully imaged.

The first and the second embodiments are explained above in a case of calculating variance of velocity components or signal strengths as statistics, the present invention is not limited to this. For example, it can be configured to calculate a maximum value of velocity components or signal strengths by same position on a plurality of calculation images as statistics, in other words, to create a maximum value image $V_{max}(r_a)$, and then to color velocity components in accordance with the calculated maximum value.

Alternatively, it can be configured such that when velocity components or signal strengths are listed in descending order of the value by same position on calculation images, an average value of velocity components or signal strengths in a certain proportion from the top (for example, in the top 10%) of the all values is calculated, and then velocity components are colored in accordance with the calculated average value. In such case, specifically, a histogram of pixel values at the same pixel is obtained from the calculation images, and then an average is calculated of pixel values within a certain proportion from the top of the all pixel values.

Although the first and the second embodiments are explained above in a case of using images imaged by an MRI apparatus, the present invention is not limited to this, and can be similarly applied to a case of using images imaged by diagnosis apparatus, for example, an X-ray Computed Tomography (CT) apparatus in other words, the present invention can be similarly applied when using a plurality of images obtained by repeating a plurality of number of times imaging that is capable of obtaining velocity components of a body fluid flowing inside a subject.

An image processing method according to the first or the second embodiment assumes a sufficient number of times of repetition of imaging, and does not assume cyclical variation in velocity, thereby easily and stably obtaining a distribution of movements on images that have not much correlation with electrocardiogram gating, such as movements of a CSF. Moreover, the image processing method uses one-shot imaging, thereby avoiding underestimating velocity variations due to the effect of average addition as a usual phase shift method doing so. Furthermore, when not performing gated imaging, the image processing method can relatively easily obtain global information about irregular movements.

Similarly to the imaging methods explained above in the first and the second embodiments, a method of obtaining an image on which a signal strength varies in accordance with a velocity is called "flow imaging". According to the first and the second embodiments, the MRI apparatus 100 performs flow imaging each time when a certain delay time elapses from each trigger signal that repeatedly appears, so as to acquire a group of echo signals required for reconstructing one image with one excitation pulse with respect to an imaging region including a CSF. The trigger signal can be an R wave of an electrocardiogram waveform, a pulse wave, or a clock signal that appears with certain intervals.

Conventionally, when performing dynamic observation of a blood flow or a heart, an MRI apparatus generally creates a plurality of images of different phases by collecting data while changing a delay time from an R wave or a pulse wave to be a trigger signal, and then continuously displays the created images.

By contrast, as described above, it is known that velocity variations of a CSF have a low correlation with electrocardiogram gating. When performing dynamic observation of a CSF, the MRI apparatus 100 according to the first or the second embodiment collects data by fixing a delay time from a trigger signal, instead of performing data collection while changing a delay time from a trigger signal as is conventionally performed. The MRI apparatus 100 then creates a plurality of CSF images that indicates dynamics of the CSF based on the collected data. When creating the images, for example, the MRI apparatus 100 continuously displays the created CSF images. Accordingly, the MRI apparatus 100 can provide images that indicate dynamics of a CSF that has a low correlation with electrocardiogram gating, to a user.

As described above, the image processing apparatus, the magnetic resonance imaging apparatus, and the image processing method according to the exemplary embodiments of the present invention are useful when observing dynamics of a body fluid flowing inside a subject, and suitable particularly when observing velocity variations that have no correlation with electrocardiogram gating, such as velocity variations of a CSF.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A magnetic resonance (MR) imaging apparatus comprising:
an MRI system having components including static and gradient magnetic field generators, at least one radio frequency (RF) coil coupled to an imaging volume, at least one RF transmitter, at least one RF receiver and at least one control computer having a processor and memory configured to control said system components so as to effect:
Time Spatial Labelling Inversion Pulse (Time-SLIP) acquisition of MR image data by repeating an imaging process a plurality of times in synchronization with a trigger signal, the imaging process including application of a labelling pulse to Cerebrospinal Fluid (CSF) flowing inside a subject, and thereafter collecting a magnetic resonance (MR) echo signal after application of an MR excitation pulse to an imaging region including the CSF;
creation of a plurality of images of labelled CSF based on echo signals collected by said repetition of the imaging process;
creation of an average value image based on the plurality of images; and
calculation of variance of signal strengths with respect to each of same positions on the plurality of images based on (a) the plurality of images and (b) the average value image.

2. The apparatus according to claim 1, wherein a group of MR echo signals used for reconstructing one image is collected by application of one excitation pulse.

3. The apparatus according to claim 2, wherein the MR echo signals are collected with a fixed delay time from application of the labelling pulse to application of the excitation pulse.

4. The apparatus according to claim 2, wherein the variance of signal strengths is calculated along a time sequence.

5. The apparatus according to claim 1, wherein the MR echo signals are collected with a fixed delay time from application of the labelling pulse to application of the excitation pulse.

6. The apparatus according to claim 1, wherein the variance of signal strengths is calculated along a time sequence.

7. The apparatus according to claim 1, wherein the trigger signal is a biological signal of the subject.

8. The apparatus according to claim 1, wherein the trigger signal is a signal generated in a fixed cycle.

9. The apparatus according to claim 1, further comprising a display configured to display a distribution of the statistics.

10. The apparatus according to claim 9, wherein the display is configured to display the distribution of the statistics by superimposing them on a certain calculation image.

11. The apparatus according to claim 9, wherein the display is configured to change a display mode of the distribution of the statistics in accordance with a value of the statistics.

12. The apparatus according to claim 9, wherein the display is configured to change a display mode of the distribution of the statistics in accordance with a flowing direction of the CSF.

13. An image processing apparatus comprising:
an MRI system having components including static and gradient magnetic field generators, at least one radio frequency (RF) coil coupled to an imaging volume, at least one RF transmitter, at least one RF receiver and at least one control computer having a processor and memory configured to control said system components so as to effect:
Time Spatial Labelling Inversion Pulse (Time-SLIP) acquisition of MR image data by obtaining a plurality of images of labelled Cerebrospinal Fluid (CSF) by repeatedly imaging according to an imaging process in synchronization with a trigger signal, the imaging process including application of a labelling pulse to CSF flowing inside a subject, and thereafter collecting a magnetic resonance (MR) echo signal after application of an excitation pulse to an MR imaging region including the CSF;
creation of an average value image based on the plurality of images; and
calculation of variance of signal strengths with respect to each of same positions on the plurality of images based on (a) the plurality of images and (b) the average value image.

14. An image processing method comprising:
using a configured magnetic resonance imaging (MRI) system to effect Time Spatial Labelling Inversion Pulse (Time-SLIP) acquisition of MR image data by obtaining a plurality of images of labelled Cerebrospinal Fluid (CSF) by repeatedly imaging according to an imaging process in synchronization with a trigger signal, the imaging process including application of a labelling pulse to CSF flowing inside a subject, and thereafter collecting an MR echo signal by application of an MR excitation pulse to an imaging region including the CSF;
creating an average value image based on the plurality of images; and calculating variance of signal strengths with respect to each of same positions on the plurality of images based on (a) the plurality of images and (b) the average value image.

\* \* \* \* \*

UNITED STATES PATENT AND TRADEMARK OFFICE
CERTIFICATE OF CORRECTION

| | | |
|---|---|---|
| PATENT NO. | : 8,903,469 B2 | |
| APPLICATION NO. | : 12/572761 | |
| DATED | : December 2, 2014 | |
| INVENTOR(S) | : Shinya Yamada et al. | |

It is certified that error appears in the above-identified patent and that said Letters Patent is hereby corrected as shown below:

On the title page under (73) Assignees, change "TOKAI UNIVERSITY EDUCATIONAL SYSTEMS" to -- TOKAI UNIVERSITY EDUCATIONAL SYSTEM --.

Signed and Sealed this
Seventeenth Day of March, 2015

Michelle K. Lee
*Director of the United States Patent and Trademark Office*